US006727240B1

(12) United States Patent
Neurath et al.

(10) Patent No.: US 6,727,240 B1
(45) Date of Patent: Apr. 27, 2004

(54) METHODS FOR PREVENTING HIV-1 OR HIV-2 INFECTION

(75) Inventors: Alexander R. Neurath, New York, NY (US); Shibo Jiang, New York, NY (US); Asim Kumar Debnath, New York, NY (US)

(73) Assignee: New York Blood Center, Inc., New York, NY (US)

( * ) Notice: Subject to any disclaimer, the term of this patent is extended or adjusted under 35 U.S.C. 154(b) by 0 days.

(21) Appl. No.: 08/342,745

(22) Filed: Oct. 21, 1994

Related U.S. Application Data

(63) Continuation-in-part of application No. 08/174,662, filed on Dec. 28, 1993.

(51) Int. Cl.[7] .............................................. A61K 31/555
(52) U.S. Cl. ........................................................ 514/185
(58) Field of Search .......................................... 514/185

(56) References Cited

U.S. PATENT DOCUMENTS

| | | | | |
|---|---|---|---|---|
| 4,692,440 A | | 9/1987 | Kappas et al. | 514/185 |
| 4,782,049 A | | 11/1988 | Kappas et al. | 514/185 |
| 5,109,016 A | * | 4/1992 | Dixon et al. | 514/410 |
| 5,230,998 A | | 7/1993 | Neurath et al. | 514/185 |

FOREIGN PATENT DOCUMENTS

| | | |
|---|---|---|
| EP | 0 199 888 | 11/1986 |
| EP | 0 337 598 | 10/1989 |
| WO | WO 89/11277 | 11/1989 |
| WO | WO 92/02242 | 2/1992 |

OTHER PUBLICATIONS

Levere, R. D. Gong, Y.–F., Kappas, A., Bucher, D. J., Wormser, G. P. & Abraham, N.G. (1991), "Heme Inhibits Human Immunodeficiency Virus 1 Replication in Cell Cultures and Enhances the Antiviral Effect of Zidovudine", *Proc. Natl. Acad. Sci. U.S.A., 88*, 1756–1759.

Drummond, G. S. & Kappas, A. (1981), Prevention of Neonatal Hyperbilirubinemia by Tin Protoporphyryin IX, a Potent Competitive Inhibitor of Heme Oxidation, *Proc. Natl. Acad. Sci., U.S.A., 78*, 6466–6470.

Kappas, A. & Drummond, G. S. (1986), "Control of Heme Metabolish With Synthetic Metalloporphyrins". *J. Clin. Invest., 77*, 335–339.

Kappas, A., Drummon, G. S. Manola, T., Petmezaki, S. & Valaes, T. (1988), "Sn–protoporphyrin Use in the Management of Hyperbilirubinemia in Term Newborns With Direct Coombs–positive ABO Incompatibility", *Pediatrics, 81*, 485–497.

Galbraith, R. A. & Kappas, A. (1989), "Pharmacokinetics of Tin–Mesoporphyrin in Man and the Effects of Tin–Chelated Porphyrin on Hyperexcretion of Heme Pathway Precursors in Patients With Acute Inducible Porphyria", *Hepatology, 9*, 882–888.

Chernick et al (1989), "Sensitivity of Human Tissue Heme Oxygenase to a New Synthetic Metalloporphyrin", *Hepatology, 10*, 365–369.

C. Miller, N. Alexander, A. Gettie, A. Hendrickx and P. Marx, (1992), "The Effect of Contraceptives Containing Nonoxynol–9 On the Genital Transmission of Simian Immunodeficiency Virus in Rhesus Macaques", *Pertility and Sterility, 57*, 1126–1128.

Lawrence K. Altman, M.D., *New York Times,* Nov. 2, 1993, pp. C–1 and C–2 "New Strategy Backed for Fighting Aids".

Neurath, A. R., Haberfield, P., Joshi, B., Hewlett, I.K., Strick, N. & Jiang, S. (1991), "Rapid Prescreening for Antiviral Agents Against HIV–1 Based on Their Inhibitory Activity in Site–Directed Immunoassays I. The V3 Loop of gp120 as Target", *Antiviral Chem. Chemother., 2*, 303–312.

Neurath, A. R., Strick, N., Haberfield, P. & Jiang, S. (1992), "Rapid Prescreening for Antiviral Agents Against HIV–1 Based on Their Inhibitory Activity in Site–Directed Immunoassays. II. Porhyrin Reacting with the V3 Loop of gp120", *Antiviral Chem. Chemother., 3*, 55–63.

Neurath, A. R., Strick, N. & Jiang, S. (1993), "Rapid Prescreening for Antiviral Agents Against HIV–1 Based on Their Inhibitory Activity in Site–Directed Immunoassays. Approaches Applicable to Epidemis HIV–1 Strains",6 *Antiviral Chem. Chemother., 4*, 207–214.

Polsky et al, 1988, The Lancet, Jan. 25 1988, Vol 8600 pp 1456.*

* cited by examiner

*Primary Examiner*—Russell Travers
(74) *Attorney, Agent, or Firm*—Frishauf, Holtz, Goodman & Chick, P.C.

(57) ABSTRACT

A method of preventing HIV-1 or HIV-2 infection by administering to a human a pharmaceutically effective anti-HIV-1 or anti-HIV-2 amount of a tin or silicon protoporphyrin IX or tin or silicon mesoporphyrin IX, or a pharmaceutically acceptable salt thereof.

12 Claims, 3 Drawing Sheets

METHODS FOR PREVENTING HIV-1 OR HIV-2 INFECTION

REFERENCE TO RELATED APPLICATION

This application is a continuation-in-part application of application Ser. No. 08/174,662, filed Dec. 28, 1993.

GOVERNMENT RIGHTS

This invention was made with United States Government support under Grant CA 43315 from the NCI. Accordingly, the United States Government has certain rights in this invention.

BACKGROUND OF THE INVENTION

1. Field of the Invention

The present invention concerns methods of preventing or treating HIV-1 or HIV-2 infection by administering to a human, especially vaginally administering to a female, a tin or silicon protoporphyrin IX or tin mesoporphyrin IX.

2. Background Information

Human immunodeficiency viruses ("HIV") have been known as the causative virus for AIDS (Acquired Immunodeficiency Syndrome). The prevalence of AIDS cases is presently increasing at an alarming rate.

Two related retroviruses that can cause AIDS are human immunodeficiency virus type 1 (HIV-1) and type 2 (HIV-2). The genomes of these two viruses are about 50% homologous at the nucleotide level, contain the same complement of genes, and appear to attack and kill the same human cells by the same mechanism.

HIV-1 was identified in 1983. Virtually all AIDS cases in the United States are associated with HIV-1 infection. HIV-2 was isolated in 1986 from West African AIDS patients.

HIV-1 and HIV-2 are retroviruses, in which the genetic material is RNA, rather than DNA. The HIV-1 and HIV-2 viruses carry with them a polymerase (reverse transcriptase) that catalyzes transcription of viral RNA into double-helical DNA.

The viral DNA can exist as an unintegrated form in the infected cell or be integrated into the genome of the host-cell. As presently understood, the HIV enters the T4 lymphocyte where it loses its outer envelope, releasing viral RNA and reverse transcriptase.

The reverse transcriptase catalyzes synthesis of a complementary DNA strand from the viral RNA template. The DNA helix then inserts into the host genome where it is known as the provirus. The integrated DNA may persist as a latent infection characterized by little or no production of virus or helper/inducer cell death for an indefinite period of time. When the viral DNA is transcribed and translated by the infected lymphocyte, new viral RNA and proteins are produced to form new viruses that bud from the cell membrane and infect other cells.

Attempts to treat AIDS with drugs which inhibit reverse transcriptase such as 3'-azido-3'-deoxythymidene (AZT) have not been met with a desirable degree of success. Moreover, there is a potential for toxicity with the use of anti-viral drugs. Thus there is a need for an effective and safe means to prevent and treat AIDS.

HIV infections are transmitted by means such as contaminated intravenous drug needles and through sexual contact. The transmission of HIV by heterosexual sex poses an especially severe problem for women. By the year 2,000, it is estimated that 90% of HIV infection will be acquired via heterosexual intercourse.

The utilization of condoms provides a substantial degree of protection against transmission of HIV infections during sexual intercourse, but a difficulty arises when condoms are not employed. Moreover, the use of condoms appears to be a culturally and socially unacceptable practice in many countries.

Although men can protect themselves from HIV infection by using condoms, women who are sexually active have no similar means. Women can encourage their male sex partners to use a condom, but may not succeed. The female condom, which is just becoming available, is expensive and there is presently no evidence that it prevents transmission of HIV.

Even maintaining a monogamous sexual relationship is no guarantee of safety, for if a woman's male partner becomes infected, he can pass the virus to her. And as more women are infected, so are more babies.

There is presently frustration in the medical field by the bleak prospect for an effective AIDS vaccine in the near future and the severe limitations of drugs that effectively and safely combat HIV.

There is a need for a safe and effective substance that can be inserted into the vagina to a foam, gel, sponge or other form to kill HIV or prevent it from infecting cells in the body. It is hoped that such substance be used by a woman without her partner's knowledge.

Several recent reports suggested the potential of porphyrins for chemotherapy of HIV-1 infections (Asanaka, M., Kurimura, T., Toya, H., Ogaki, J. & Kato, Y., (1989), "Anti-HIV Activity of Protoporphyrin", *AIDS*, 3, 403–404; Levere, R. D. Gong, Y.-F., Kappas, A., Bucher, D. J., Wormser, G. P. & Abraham, N. G. (1991), "Heme Inhibits Human Immunodeficiency Virus 1 Replication in Cell Cultures and Enhances the Antiviral Effect of Zidovudine", *Proc. Natl. Acad. Sci. U.S.A.*, 88, 1756–1759; Dixon, D. W. Schinazi, R. & Marzilli, L. G., (1990), "Porphyrin As Agents Against the Human Immunodeficiency Virus." *Ann N.Y. Acad. Sci.*, 616, 511–513; and Dixon, D. W., Kim, M. S., Kumar, V., Obara, G., Marzilli, L. G. & Schinazi, R. F. (1992), "Amino- and Hydroxytetraphenylporphyrins with Activity Against the Human Immunodeficiency Virus.", *Antiviral Chem. Chemother.*, 3, 279–282).

Porphyrin derivatives competitively inhibiting HIV-1 protease have been designed (DeCamp, D. L., Babé, L. M., Salto, R., Lucich, J. L., Koo, M.-S., Kahl, S. B. & Craik, C. S. (1992), "Specific Inhibition of HIV-1 Protease by Boronate Porphyrin", *J. Med. Chem.*, 35, 3426–3428). The effect of these compounds on HIV-1 replication has not been reported. The predominant binding of some porphyrins to the V3 loop of the HIV-1 envelope glycoprotein gp120, and a correlation between the V3 loop binding capacity of some porphyrins and their antiviral activity have been recently demonstrated (Neurath, A. R., Haberfield, P., Joshi, B., Hewlett, I. K., Strick, N. & Jiang, S. (1991), "Rapid Prescreening for Antiviral Agents Against HIV-1 Based on Their Inhibitory Activity in Site-Directed Immunoassays I. The V3 Loop of gp120 as Target," *Antiviral Chem. Chemother.*, 2, 303–312; Neurath, A. R., Strick, N., Haberfield, P. & Jiang, S. (1992), "Rapid Prescreening for Antiviral Agents Against HIV-1 Based on Their Inhibitory Activity in Site-Directed Immunoassays. II. Porphyrin Reacting with the V3 Loop of gp120", *Antiviral Chem. Chemother.*, 3, 55–63; and Neurath, A. R. (1993), "B Cell Antigenic Site Mapping of HIV-1 Glycoproteins. In: Immunochemistry of AIDS", *Chemical Immunology*, Vol. 56, E. Norrby ed.), pp. 34–60, Karger, Basel; Neurath, A. R., Strick, N. & Jiang, S. (1993), "Rapid Prescreening for Antiviral Agents Against HIV-1 Based on Their Inhibitory Activity in Site-Directed Immunoassays. Approaches Applicable to Epidemic HIV-1 Strains", *Antiviral Chem. Chemother.*, 4, 207–214; and U.S. Pat. No. 5,230,998, the entire contents of U.S. Pat. No. 5,230,998 being incorporated by reference herein).

Levere , R. D., Gong, Y-F., Kappas, A., Bucher, D. J., Wormser, G. P. and Abraham, N. G., (1991), "Heme Inhibits Human Immunodeficiency Virus 1 Replication In Cell Cultures and Enhances the Antiviral Effect of Zidovodine", *PNAS*, 88, 1756–1759 concern the study of heme alone and heme together with AZT, on HIV replication in human peripheral blood lymphocytes and in the H9 cell line. The following is noted with respect of Levere et al:

(1) The Levere et al results did not achieve substantial suppression of viral infection using only a metalloporphyrin;

(2) Levere et al report only relatively low activity using heme;

(3) The thrust of Levere et al is to use heme in conjunction with AZT.

WO 89/11277 and U.S. Pat. No. 5,109,016 to Dixon, Schinazi and Marzilli concern a method for inhibiting infection or replication of human immunodeficiency virus comprising administering an effective amount of a porphyrin, porphyrin-like compound or a derivative thereof to inhibit HIV infection in cells.

U.S. Pat. No. 5,109,016 describes the following metals which can be inserted into the tetrapyrrole ring of porphyrin: Fe, Co, Zn, Mo, Ti, Mn, Cr, Ni, Mg, Cu, Tl, In, Ru, V and Au, however, Sn is not described in U.S. Pat. No. 5,109,106.

U.S. Pat. No. 5,109,016 indicates that their results demonstrate that non-metalloporphyrins are generally more active than the metalloporphyrins.

EP 337,598 describes the use of porphyrin and metalloporphyrins to treat diseases caused by HIV.

EP 337,598 describes the following metal coordination compounds of the porphyrin: Mg, Fe (II) (e.g., Heme), Fe (III), FeCl (e.g., Hemin), Co and Cu.

EP 337,598 does not describe tin protoporphyrins.

Levere et al (1991), *PNAS*, 88, 1756–1759; WO 89/11277; U.S. Pat. No. 5,109,106 and EP 337,598 concern only porphyrin interaction with HIV infected cells, i.e., cells after infection or post-infection. Thus these publications concern only intracellular events, e.g., replication, and are not directed to the prevention of HIV-1 or HIV-2 infection.

Porphyrins having anti-HIV-1 activity in in vitro assays have so far not been tested for antiviral activity in vivo. The correlation between in vitro and in vivo efficacy of spermicide nonoxynol-9 to prevent the genital transmission of simian immunodeficiency virus (SIV"), a nonhuman primate lentivirus that is closely related to HIV-2, was discussed in C. Miller, N. Alexander, A. Gettie, A. Hendrickx and P. Marx, (1992), "The Effect of Contraceptives Containing Nonoxynol-9 On the Genital Transmission of Simian Immunodeficiency Virus in Rhesus Macaques", *Fertility and Sterility*, 57, 1126–1128. Since Sn-PTP-IX prevents HIV infection in vitro it is considered that these results support the efficacy of local application of Sn-PTP-IX.

The tin complex of protoporphyrin IX (Sn-PTP-IX) is known for use in control of heme metabolism in humans and specifically for suppression of hyperbilirubinemia (Drummond, G. S. & Kappas, A. (1981), "Prevention of Neonatal Hyperbilirubinemia by Tin Protoporphyryin IX, a Potent Competitive Inhibitor of Heme Oxidation, *Proc. Natl. Acad. Sci., U.S.A.*, 78, 6466–6470; Kappas, A., Drummond, G. S., Simionatto, C. S. & Anderson, K. E. (1984), "Control of Heme Oxygenase and Plasma Levels of Bilirubin by a Synthetic Heme Analogue, Tin-protoporphyrin", *Hepatology*, 4, 336–341; Kappas, A. & Drummond, G. S. (1986), "Control of Heme Metabolism With Synthetic Metalloporphyrins". *J. Clin. Invest.*, 77, 335–339; Anderson, K. E., Simionatto, C. S., Drummond, G. S. & Kappas, A. (1986), "Disposition of Tin-Protoporphyrin and Suppression of Hyperbilirubinemia in Humans", *Clin. Pharmacol. Ther.*, 39, 510–520; Kappas, A., Drummond, G. S. Manola, T., Petmezaki, S. & Valaes, T. (1988), "Sn-protoporphyrin Use in the Management of Hyperbilirubinemia in Term Newborns With Direct Coombs-positive ABO Incompatibility", *Pediatrics*, 81, 485–497; Berglund, L., Angelin, B., Blomstrand, R., Drummond, G & Kappas, A. (1988), "Sn-protoporphyrin Lowers Serum Bilirubin Levels, Decreases Biliary Bilirubin Output, Enhances Biliary Heme Excretion and Potently Inhibits Hepatic Heme Oxygenase Activity in Normal Human Subjects", *Hepatology*, 8, 625–631; Galbraith, R. A. & Kappas, A. (1989), "Pharmacokinetics of Tin-Mesoporphyrin in Man and the Effects of Tin-Chelated Porphyrin on Hyperexcretion of Heme Pathway Precursors in Patients With Acute Inducible Porphyria", *Hepatology*, 9, 882–888; Chernick et al (1989), "Sensitivity of Human Tissue Heme Oxygenase to a New Synthetic Metalloporphyrin", *Hepatology*, 10, 365–369 and EP 199, 888 to Kappas and Drummond).

Sn-PTP-IX has been heretofore employed for control of psoriasis (Emtestam, L., Berglund, L., Angelin, B., Drummond, G. S. & Kappas, A. (1989), "Tin-protoporphyrin and Long Wave Length Ultraviolet Light in Treatment of Psoriasis". *Lancet i*, 1231–1233 and Emtestam, L., Angelin, B., Berglund, L., Drummond, G. S. & Kappas, A. (1993), "Photodynamic Properties of Sn-protoporphyrin: Clinical Investigations and Phototesting in Human Subjects", *Acta. Derm. Venereol.* (*Stockh*), 73, 26–30).

The use of Sn-PTP-IX has also been discussed in the following publications: Stevenson, D. K., Rodgers, P. A. & Vreman, H. J. (1989), "The Use of Metalloporphyrins for the Chemoprevention of Neonatal Jaundice", *Am. J. Dis. Child*, 143, 353–356; Maines, M. D. & Trakshel, G. M. (1992), "Tin-protoporphyrin: A Potent Inhibitor of Hemoprotein-Dependent Steroidogenesis in Rat Adrenals and Testes", *J. Pharmacol. Exp. Their.*, 260, 909–916; and Mark, J. A. & Maines, M. D. (1992), "Tin-protoporphyrin-mediated Disruption In Vitro of Heme Oxygenase-2 Protein Integrity and Activity in Rat Brain", *Pediatric Research*, 32, 324–329).

The combination of Sn-PTP-IX with 1-ascorbic acid may decrease potential phototoxic side effects (Keino, H., Mimura, S., Nagae, H., Banno, T. & Kashiwamata, S. (1993), "Protection By L-ascorbic Acid Against Phototoxicity in Tin-protoporphyrin-treated Suckling Rats", *Biol. Neonate*, 63, 183–190).

Sn-PTP-IX was shown to have immunostimulatory Effects in vitro and to enhance the biological activity of γ-interferon (Novogrodsky, A., Suthanthiran, M. & Stenzel, K. H. (1989), "Immune Stimulatory Properties of Metalloporphyrins", *J. Immunol.*, 143, 3981–3987 and Weiss, G., Lutton, J. D., Fuchs, D., Werner-Felmayer, G., Bock, G., Abraham, N. G. Kappas, A., Levere, R. D. & Wachter, H. (1993), "Comparative Effects of Heme and Metalloporphyrins on Interferon-γ-mediated Pathways in Monocytic Cells (THP-1)", *Proc. Soc. Exp. Biol. Med.*, 202, 470–475).

Tin complexes of porphyrin have not heretofore been tested for anti-HIV-1 activity. Protoporphyrin IX has been shown to be a compound with desirable anti-HIV-1 activity (Neurath et al., (1992), *Antiviral Chem. Chemother.*, 3, 55–63).

In contrast to Sn-PTP-IX, Zn-PTP-IX has approximately 50 times higher $ED_{50}$ values than Sn-PTP-IX (Trakshel, G. M., Sluss, P. M. & Maines, M. D. (1992), "Comparative Effects of Tin- and Zinc-protoporphyrin on Steroidogenesis: Tin-protoporphyrin is a Potent Inhibitor of Cytochrome P-450-dependent Activities in the Rat Adrenals", *Pediatric Research*, 31, 196–201).

Heretofore there has been a prejudice in the art against utilizing metal complexes in view of the earlier observation that other metal complexes (Co, Cr, Cu, Fe, Mn, Ni and Zn, respectively) of porphyrin have low, if any, anti-HIV-1 antiviral activity (Neurath et al (1992), *Antiviral Chem. Chemother.*, 3, 55–63). Fe-PTP-IX (hemin) has been shown to have low anti-HIV-1 activity ($ED_{50}$=23 $\mu$g/ml) similar to the activity of other metal derivatives of PTP-IX which have so far been tested. In general, the prior art teaches that metal-porphyrin complexes have significantly lower anti-HIV activity than the corresponding uncomplexed porphyrin.

SUMMARY OF THE INVENTION

It is an object of the present invention to provide a method to prevent HIV-1 or HIV-2 infection and more particularly to prevent vaginal and anal transmission of HIV-1 or HIV-2 during sexual intercourse or vaginal transmission during childbirth.

It is another object of the present invention to provide a method to treat humans suffering from HIV-1 or HIV-2 infection.

The aforesaid objects, as well as other objects, aims and advantages are satisfied by the present invention.

The present invention concerns a method of preventing or treating HIV-1 or HIV-2 infection by administering to a human a pharmaceutically effective anti-HIV-1 or anti-HIV-2 amount of a tin or silicon protoporphyrin IX or a tin or silicon mesoporphyrin IX, or a pharmaceutically acceptable salt thereof, alone or in admixture with a pharmaceutically acceptable diluent (carrier).

The present invention also provides a method of preventing transmission of HIV-1 infection or HIV-2 infection which comprises locally administering to an appropriate region of a human body a pharmaceutically effective anti-HIV-1 or anti-HIV-2 amount of tin or silicon protoporphyrin IX or tin or silicon mesoporphyrin IX or a pharmaceutically acceptable salt thereof. Such method is intended to prevent transmission of HIV infection, for example, during close bodily contact between two individuals under conditions which would generally favor HIV transmission, for example, during sexual intercourse or during childbirth.

The phrase "administration to an appropriate region of the human body" includes, for example, application of tin protoporphyrin IX or tin mesoporphyrin IX to regions of the human body which come into close contact with another human body, for example, application to the male or female genitalia if the method is intended to prevent transmission during sexual intercourse, and application to the vagina or to a baby's epidermis if the method is intended to prevent transmission during childbirth.

The term "locally administrating" includes any method of administration in which the activity of the tin protoporphyrin IX is substantially confined to the region of the human body to which it is applied, for example, vaginal, rectal or topical administration.

The present invention thus provides a method of preventing vaginal transmission of HIV-1 or HIV-2, either during sexual intercourse or during childbirth (vaginal delivery), by vaginal administration, such as by administering a cream, ointment, lotion, jelly, solution, emulsion or foam formulation containing a pharmaceutically effective anti-HIV-1 or anti-HIV-2 amount of tin or silicon protoporphyrin IX or tin or silicon mesoporphyrin IX.

The present invention also therefore relates to a method of preventing transmission of HIV-1 or HIV-2 in a newborn baby by topically administering to the baby soon after childbirth a pharmaceutically effective anti-HIV-1 or anti-HIV-2 amount of a tin or silicon protoporphyrin IX or tin or silicon mesoporphyrin IX, either alone or in combination with a carrier.

The present invention is also directed to a contraceptive device (for example, a male or female condom, a contraceptive diaphragm or a contraceptive sponge, for example, a polyurethane foam sponge), for the prevention of pregnancy, the improvement comprises said device having applied thereto an anti-HIV-1 or anti-HIV-2 effective amount of tin or silicon protoporphyrin IX or tin or silicon mesoporphyrin IX or a pharmaceutically acceptable salt thereof.

The present invention also relates to a pharmaceutical composition comprising, as active ingredients, (i) a pharmaceutically effective anti-HIV-1 or anti-HIV-2 amount of tin or silicon protoporphyrin IX or tin or silicon mesoporphyrin IX or a pharmaceutically acceptable salt thereof and (ii) an effective spermicidal amount of one or more spermicidal agents, for example, nonoxynol-9, benzalkonium chloride, menfegol, gossypol, chlorohexidine and "BETADINE" (povidone-iodine) alone or in association with at least one pharmaceutical carrier and/or excipient.

The present invention is further directed to a pessary or tampon for vaginal administration, wherein the tampon or pessary comprises, as an active ingredient, a pharmaceutically effective anti-HIV-1 or anti-HIV-2 amount of tin or silicon protoporphyrin IX or tin or silicon mesoporphyrin IX or a pharmaceutically acceptable salt thereof and one or more pharmaceutically acceptable carriers or excipients.

The present invention further relates to a pharmaceutical composition for topical administration comprising a pharmaceutically effective anti-HIV-1 or anti-HIV-2 amount of tin or silicon protoporphyrin IX or tin or silicon mesoporphyrin IX, or a pharmaceutically acceptable salt thereof and at least one pharmaceutically acceptable topical carrier or excipient, to form an ointment, cream, gel, lotion, paste, jelly, spray or foam.

BRIEF DESCRIPTION OF THE DRAWINGS

FIG. 1A is a graph which shows the inhibitory effect of graded quantities of Sn-PTP-IX on infection by HIV-1 IIIB of MT-2 cells. FIG. 1B is a bar graph which shows the concentrations of Sn-PTP-IX at which the production of the HIV-1 nucleocapsid antigen p24 or the cytopathogenic effects (CPE) were 50% of those detected in virus infected cultures in the absence of Sn-PTP-IX for different HIV-1 strains indicated on the abscissa.

DETAILED DESCRIPTION OF THE INVENTION

Figure 1A:
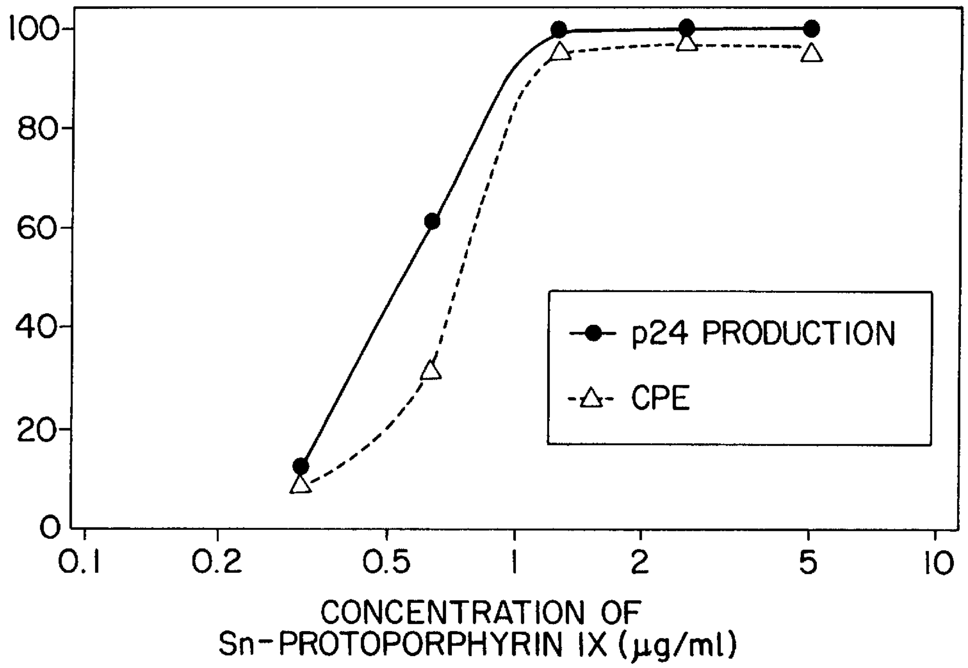
FIGS. 1A and 1B are graphs which show the inhibition of Sn-protoporphyrin IX (Sn-PTP-IX) of MT-2 cell infection by HIV-1.

Porphyrins and porphyrin-like compounds, such as phthalocyanines, are tetrapyrrole macrocycle compounds with bridges of one carbon or one nitrogen joining the pyrroles. The term porphyrin is used herein to mean porphyrins, phthalocyanines, chlorins and other porphyrin-like compounds, unless otherwise stated.

Many porphyrins are isolated from nature, for example, protoporphyrin IX, which is the organic portion of hemin, while many other porphyrins and phthalocyanines can be made synthetically.

Many derivatives of natural porphyrins are known (see, for example Smith and Cavaleiro (1988), "Protoporphyrin-IX: Some Useful Substituent Manipulations", *Heterocycles*, 26, 1947–1963).

The protoporphyrin IX compounds for use in the present invention are of the following formulae:

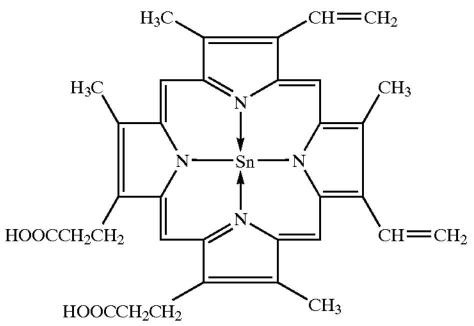

Sn (IV) Protoporphyrin IX

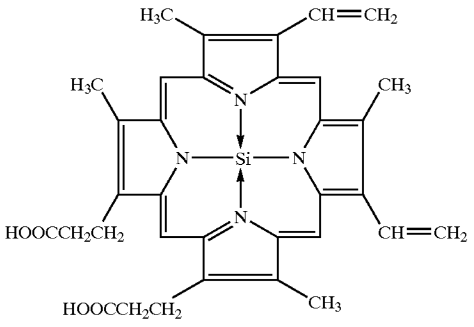

Si (IV) Protoporphyrin IX

Sn-PTP-IX, as well as other porphyrins, bind both to the V3 loop of gp120 and to the gp120 binding site of the HIV-1 receptor, CD4. Thus, without wishing to be bound by any particular therapy of operability, it is considered that the anti-HIV-1 activity of these compounds could be ascribed to either of these binding capacities. The overlap between the V3 loop and CD4 binding properties of a series of porphyrin and non-porphyrin compounds suggests the possibility of structural similarities between portions of the gp120 V3 loop and the gp120 binding site for CD4 involved in binding of anti-CD4 mAb Leu3a.

It has previously been observed by Neurath et al (Neurath et al (1992) *Antiviral Chem. Chemother.*, 3, 55–63; Neurath et al (1993), *Antiviral Chem. Chemother.*, 4, 207–214) that the $ED_{50}$ values for certain porphyrins differ for HIV-1 strains having distinct V3 loop amino acid sequences. A similar observation has now been made in relation to the $ED_{50}$ values of Sn-PTP-IX. It is considered that the emergence of HIV-1 variants resistant to the antiviral effects of compounds targeted to the V3 loop is less likely than resistance to antiviral compounds targeted to HIV-1 revere transcriptase or protease (Larder, B. A., Kellam, P. & Kemp, S. D. (1993), "Convergent Combination Therapy Can Select Viable Multidrug-Resistance HIV-1 in vitro", *Nature*, 365, 451–453).

The antiviral effect of Sn-PTP-IX is considered to be predominant during early stages of infection and is likely to be diminished if the compounds are administered to already infected cells. Thus Sn-PTP-IX is considered to inhibit the process of virus-cell fusion and of fusion of uninfected cells with infected cells.

Applicants discovered that surprisingly, Sn-PTP-IX effectively inhibited HIV-1 infection at considerably lower concentrations than did metal-free PTP-IX. This finding is in direct contradiction with the prior art teaching that metal-porphyrin complexes generally have drastically reduced anti-HIV activity compared to the activity of the corresponding metal-free prophyrin. This finding was also unexpected, since Sn-PTP-IX binds more weakly to several porphyrin binding proteins than porphyrin complexes with other metals (Breslow, E., Chandra, R. & Kappas, A. (1986), "Biochemical Properties of the Heme Oxygenase Inhibitor, Sn-protoporphyrin. Interactions with Apomyoglobin and Human Serum Albumin", *J. Biol. Chem.*, 261, 3135–3141; Dailey, H. A., Jones, C. S. & Karr, S. W. (1989), "Interaction of Free Porphyrin and Metalloporphyrins with Mouse Ferrochelatase". A Model for the Active Site of Ferrochelatase., *Biochim. Biophys. Acta*, 999, 7–11).

Without wishing to be bound by any particular theory of operability, it is considered that the exceptional antiviral properties of the tin porphyrin may possibly be related to the unique coordination properties of the $Sn^{4+}$ cation reflected in the extraordinary stability of Sn-porphyrin complexes against oxidation, their ease to undergo reduction and nucleophilic additions to the porphyrin macrocycle and a decreased availability of ring electrons (Fuhrhop, J.-H. & Lumbantobing, T. (1970), "The Redox Properties of Tin (IV) and Germanium (IV)-Octaethyl Porphinato-Dihydroxide as Compared to Other Metallo-Octaethylporphins", *Tetrahedron Letters*, 32, 2815–2818 and Breslow et al (1986), *J. Biol. Chem.*, 21, 3135–3141). These properties of Sn-PTP-IX may be related to its high inhibitory activity against heme oxygenase which led to its clinical application for suppression of bilirubinemia (Breslow et al (1986), *J. Biol. Chem.*, 21, 3135–3141).

The HIV-1 inhibitory activity of protoporphyrin IX and Co, Zn and Mn complexes thereof, including tin protoporphyrin IX, and tin mesoporphyrin IX are shown in the following Table 1.

TABLE 1

HIV-1 inhibitory activity of Protoporphyrin IX and metal complexes thereof and Tin Mesoporphyin IX

| Porphyrin derivative tested | $CD_{50}$[a] ($\mu g/ml^{-1}$) | $ED_{50}$[b] ($\mu g/ml^{-1}$) | S.I.[c] |
|---|---|---|---|
| 1 Sn-Protoporphyrin IX | 18.0 | 0.54 | 33.5 |
| 2 Protoporphyrin IX | 8.9 | 1.22 | 7.3 |
| 3 Co-Protoporphyrin IX | >80 | 12.93 | >6.2 |
| 4 Zn-Protoporphyrin IX | >80 | 26.04 | >3.1 |
| 5 Mn-Protoporphyrin IX | >80 | 28.67 | >2.8 |
| 6 Sn-Mesoporphyrin IX | >20 | 3.578 ± .251 | >5.6 |

Notes:
[a]$CD_{50}$ = concentration at which 50% of uninfected cells were lysed.
[b]$ED_{50}$ = concentration at which the production of p24 was reduced to 50% of that detected in HIV-1-infected cultures in the absence of porphyrins.
[c]S.I. = selectivity index = $CD_{50}/ED_{50}$(toxicity/activity)

Pharmaceutically acceptable salts of the above described compounds (drugs) to treat or prevent HIV-1 or HIV-2 according to the invention include those derived from pharmaceutically acceptable inorganic acids and bases. Examples of suitable acids include hydrochloric, hydrobromic, sulfuric, nitric, perchloric, fumaric, maleic, phosphoric, glycollic, lactic, salicylic, succinic, toluene-p-sulfonic, tartaric, acetic, citric, methanesulfonic, formic, benzoic, malonic, naphthalene-2-sulfonic and benezene-sulfonic acids.

As used herein, the term "active ingredient" includes the compound (drug) itself, as well as a salt thereof.

Salts derived from appropriate bases include alkali metal (e.g., sodium), alkaline earth metal (e.g., magnesium), ammonium and $NR_4^+$ (where R is $C_{1-4}$ alkyl) salts.

The amount of the active ingredient for use in the present invention will vary, not only with the particular compound selected, but also with the route of administration, whether prevention or treatment is sought, and the age and condition of the patient and will be ultimately determined by the discretion of the attendant physician. In general, however, a suitable concentration of Sn-PTP-IX or tin mesoporphyrin IX in a topical dosage form is up to 100 micrograms of Sn-PTP-IX or tin mesoporphyrin IX per milliliter, preferably between 2 and 100, and more preferably 25 to 50, micrograms of Sn-PTP-IX or tin mesoporphyrin IX per milliliter.

The desired dose may conveniently be presented in a single dose or as divided doses administered at appropriate intervals, for example, at two, three, four or more sub-doses per day.

While it is possible that the active ingredient may be administered as the raw chemical, it is preferable to present the active ingredient in conjunction with a pharmaceutically acceptable diluent (carrier) as a pharmaceutical formulation.

The invention thus further provides for the use of a pharmaceutical formulation comprising an active ingredient together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient therefor.

Pharmaceutical formulations include those suitable for vaginal, oral, rectal, nasal, topical (including buccal and sub-lingual) or parenteral (including intramuscular, subcutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active ingredient with liquid carriers or finely divided solid carriers or both and then, if necessary, shaping the product into the desired formulation.

Formulations suitable for vaginal administration may be presented as pessaries, tampons, creams, gels, pastes, jelly, foams or sprays or aqueous or oily suspensions., solutions or emulsions (liquid formulations) containing in addition to the active ingredient, such carriers as are known in the art to be appropriate. These formulations are useful to protect not only against sexual transmission of HIV, but also to prevent infection of a baby during passage through the birth canal. Thus the vaginal administration can take place prior to sexual intercourse, during sexual intercourse, immediately prior to childbirth or during childbirth.

As a vaginal formulation, the active ingredient may be used in conjunction with a spermicide and may be employed with condoms, diaphragms, sponges or other contraceptive devices.

Pharmaceutical formulations suitable for oral administration may conveniently be presented as discrete units such as capsules, cachets or tablets each containing a predetermined amount of the active ingredient; as a powder or granules; as a solution; as a suspension; or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspension, solutions, emulsions, syrups or elixirs, or may be presented as a dry product for constitution with water or other suitable vehicle before use. Liquid preparations for oral or vaginal administration may contain conventional additives such as suspending agents, emulsifying agents, non-aqueous vehicles (which may include edible oils) or preservatives.

The active ingredient may also be formulated for parental administration (e.g., by injection, for example, bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the active ingredient may be formulated as an ointment, cream, paste, jelly, foam, gel or lotion, or as a transdermal patch for topical administration. Ointments, pastes, jellies, liquids, foams, gels and creams may, for example, be formulated with an aqueous or oil base with the addition of suitable thickening and/or gelling agents. Lotions may be formulated with an aqueous or oil base and will in general also contain one or more emulsifying agents, stabilizing agents, suspending agents, thickening agents, or coloring agents. Such topical dosage forms may be particularly useful when applied to a newborn baby of an HIV-infected mother.

Formulations suitable for topical administration in the mouth include lozenges comprising an active ingredient in a flavored base, usually sucrose and acacia or tragacanth; or pastilles comprising the active ingredient in a suitable liquid carrier.

Pharmaceutical formulations suitable for rectal administration, wherein the carrier is a solid, are most preferably represented as unit dose suppositories. Suitable carriers include cocoa butter and other materials commonly used in the art, and the suppositories may be conveniently formed by admixture of the active compound with the softened or melted carrier(s) followed by chilling and shaping in molds.

For intra-nasal administration, the active ingredient may be used as a liquid spray or dispersible powder or in the form of drops.

Drops may be formulated with an aqueous or non-aqueous base comprising one or more dispersing agents, solubilizing agents or suspending agents. Liquid sprays are conveniently delivered from pressurized packs.

For administration by inhalation, the active ingredient is conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the active ingredient may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

When desired, the above described formulations adapted to give sustained release of the active ingredient may be employed.

The pharmaceutical compositions for use according to the invention may also contain other active ingredients such as spermicides as discussed above, or antimicrobial agents or preservatives.

The active ingredient may also be used in combination with other therapeutic agents, for example, other anti-infective agents.

The combinations referred to above may conveniently be presented for use in the form of a pharmaceutical formulation and thus the use of pharmaceutical formulations comprising a combination as defined above together with a pharmaceutically acceptable carrier therefor comprise a further aspect of the invention.

The individual components of such combinations may be administered either sequentially or simultaneously in separate or combined pharmaceutical formulations.

When a compound (drug) as described herein is used in combination with a second therapeutic, the dose of each compound may be either the same or different from that when the analog is used alone. The appropriate dose will be readily appreciated by those skilled in the art.

EXAMPLES

Example 1

Screening of Protoporphyrin IX (PTP-IX) and its Metal Complexes for Antiviral Activity PTP-IX and its metal complexes (Sn, Co, Zn, Mn) were obtained from Porphyrin Products, Inc., Logan, Utah, USA.

They were obtained from Porphyrin Products, Inc., Logan, Utah, USA. They were tested for antiviral activity at serial two-fold dilutions (0.16–80 μg/ml$^{-1}$). Their inhibitory activity was determined based on inhibition of synthesis of the HIV-1 core protein p24 and on protection by the compounds of cells against the cytopathic effect of HIV-1. The cytotoxic effect of all compounds in the absence of HIV-1 was also determined.

Figure 1B:
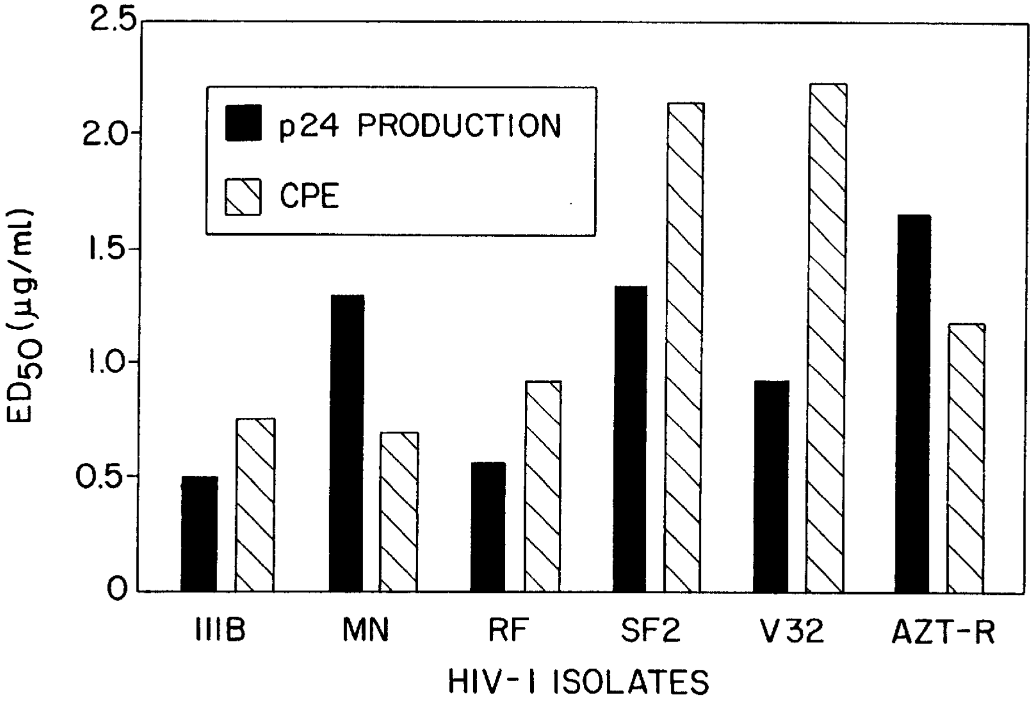

The antiviral activity of the compounds was tested against HIV-1 IIIB, MN, RF and SF-2, as well as against azidothymidine (AZT) resistant variants V32 (Nara, P. L., Smit, L., Dunlop, N., Hatch, W., Merges, M., Waters, D. Kelliher, J., Gallo, R. C., Fischinger, P. J. & Goudsmit, J. (1990), "Emergence of Viruses Resistant to Neutralization by V3-specific Antibodies in Experimental Human Immunodeficiency Virus Type 1 IIIB Infection of Chimpanzees, *J. Virol*., 64, 3779–3791) and AZT-R (see FIG. 1B). The HIV-1 strains, except V32, were obtained from AIDS Research and Reference Reagent Program.

The methods for detection of core protein p24 and of cytopathic effects were the same as described in Neurath et al (1991), *Antiviral Chem. Chemother*., 2, 303–312 and Neurath et al (1992), *Antiviral Chem. Chemother*., 3, 55–63. Such methods are as follows:

All chemicals were tested at serial two-fold dilutions (1.25–80 μgml$^{-1}$, prepared from a stock solution containing 10 mgml$^{-1}$ in dimethylsulphoxide). The chemicals were obtained from Aldrich, Milwaukee, Wis. or were synthesized. Their inhibitory activity was determined by two distinct methods, based on inhibition of synthesis of core protein p24 and on protection by the chemicals of cells against the cytophathic effect of HIV-1 (colorimetric method), respectively.

The chemicals were serially diluted in RPMl-1640 medium without phenol red (Gibco, Grand Island, N.Y.) containing 10% fetal calf serum (FCS). Aliquots of the diluted solutions were added to wells of 96-well plates and mixed with an equal volume of diluted HIV-1 [multiplicity of infection (MOl)=0.0045]. After incubation for 1 hour at 37° C., 25 μl of polybrene (1 μgml$^{-1}$)-treated MT-2 cells (Harada et al., (1985), "Infection of HTLV-III/LAV in HTLV-1-Carrying Cells MT-2 and MT-4 and Application in Plaque Assay", *Science*, 229, 563–566) (5000 cells/well) were added. The mixture was incubated for 1 hour at 37° C. and the volume was adjusted with RPMl-1640 medium with 10% FCS to 200 μl. On the fourth and sixth day after incubation at 37° C., 100 μl of culture supernatants were collected from each well and equal volumes of fresh medium were added to the wells. The supernatants were collected from each well and equal volumes of fresh medium were added to the wells. The supernatants were assayed for p24 using a kit from Coulter Immunology (Hialeah, Fla.). On the sixth day, an indicator, XTT tetrazolium dye (1 mg/ml:50 μl/well; PolySciences, Inc., Warrington, Pa.) was added to the cells. After 4 hours intracellular formazan was determined colorimetrically at 450 nm.

Example 2

Inhibitory Effect of PTP-IX and its Metal Complexes in the Reaction Between gp120 and Antibodies Specific for the V3 Hypervariable Loop or for the CD4 Binding Site on gp120

The inhibitory effect of PTP-IX and its metal derivatives on binding to gp120 of monoclonal antibodies (mAbs)

specific for the V3 loop or for the CD4 binding site was measured by ELISA tests using as second antibodies horseradish peroxidase (HRP) labeled anti-mouse IgG. The tests were performed as described in Neurath et al (1991), *Antiviral Chem. Chemother.*, 2, 303–312 and Neurath et al (1992), *Antiviral Chem Chemother.*, 3, 55–63 and as set forth hereinabove.

Figure 2:
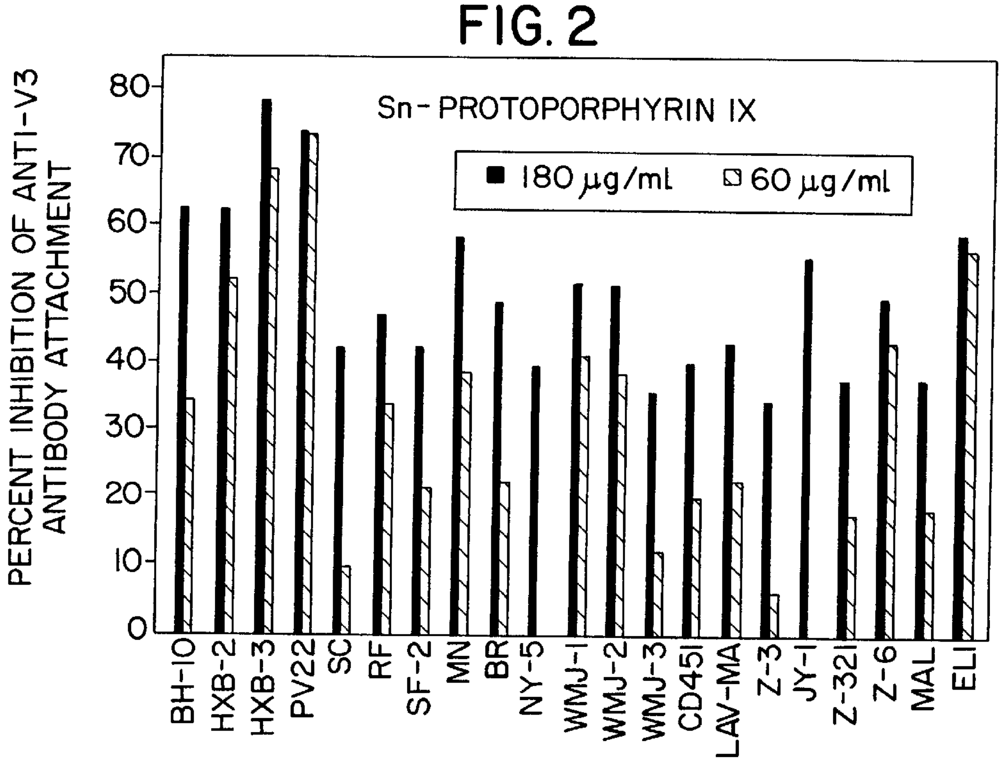
FIG. 2 is a bar graph which shows the inhibitory effect of tin protoporphyrin IX on the reaction of full-length V3 hypervariable loop peptides from gp120 from 21 distinct HIV-1 isolates (clones) with homologous anti-peptide antisera.

Sn-PTP-IX was also tested for inhibition of the reaction between V3 hypervariable loop peptides from 21 distinct HIV-1 isolates and the corresponding homologous antipeptide antibodies. These tests were carried out as described in Neurath et al (1991), *Antiviral Chem. Chemother.*, 2, 303–312 and as set forth hereinabove. The results are shown in FIG. 2. With respect of FIG. 2, peptide coated wells of polystyrene plates were reacted in the presence and absence of the porphyrin derivative with the respective rabbit antisera diluted 1:1,000, and the attachment of rabbit IgG was subsequently determined using horseradish peroxidase labeled anti-rabbit IgG.

The results shown in FIG. 2 indicate that Sn-PTP-X inhibited the reaction between respective peptides and the homologous antibodies.

Figure 3:
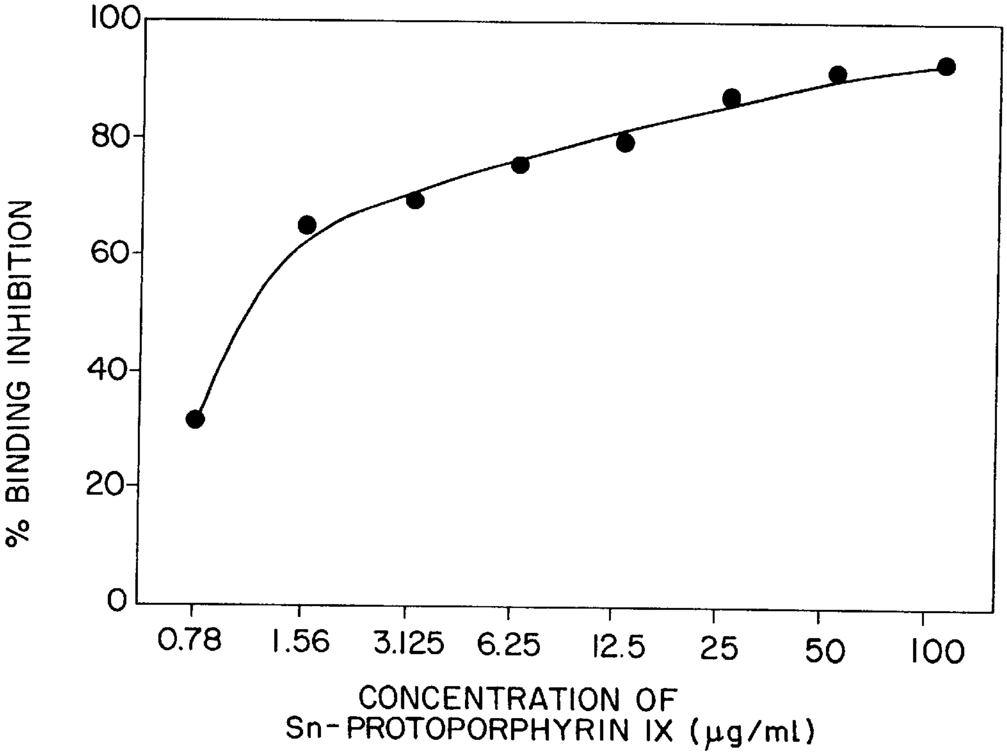
FIG. 3 is a graph which demonstrates the inhibitory effect of graded quantities of the tin derivative of protoporphyrin IX on binding to gp120-coated wells of mAB 588D (200 ng/well), specific for the CD4 binding site of gp120.

The inhibitory effect of Sn-PTP-IX on the reaction between gp120 and mAb specific for the CD4 binding site on gp120 was also investigated. For this purpose, mAb 588D (obtained from the AIDS Research and Reagent Reference Program and from Dr. S. Zolla-Pazner of New York Veterans Affairs Medical Center) was used. The results are shown in FIG. 3.

The inhibitory effect of PTP-IX and its metal complexes on the reaction between antibodies of distinct specificities and gp120 (or synthetic peptides derived from it) was calculated by the following formula:

$$\frac{[\text{optical density at 450 nm } (OD_{450}) \text{ in the absence of } PTP\text{-}IX \text{ derivatives } (PTP\text{-}IX\text{-}D)] - [OD_{450} \text{ in presence of } PTP\text{-}IX\text{-}D]}{[OD_{450} \text{ in the absence of } PTP\text{-}IX\text{-}D]}$$

Sn-PTP-IX blocked in a concentration dependent manner the binding of mAb 588D, specific for the CD4 binding site on gp120corresponding to a discontinuous epitope. (Thali, M., Olshevsky, U., Furman, C., Gabuzda, D., Posner, M. & Sodroski, J. (1991) "Characterization of a Discontinuous Human Immunodeficiency Virus Type 1 gp120 Epitope Recognized by a Broadly Reactive Neutralizing Human Monoclonal Antibody," *J. Virol.*, 65, 6188–193; Pollard, S. R. Rosa, M. D., Rosa, J. J. & Wiley, D. C. (1992), "Truncated Variants of gp120 Bind CD4 With High Affinity and Suggest a Minimum CD4 Binding Region," *EMBO J.*, 11 585–591, Neurath et al (1992), *Virology*, 188, 1–13; Laal, S. & Zolla-Pazner, S. (1993), "Epitopes of HIV-1 Glycoproteins Recognized by the Human Immune System", In: *Immunochemistry of AIDS, Chemical Immunology*, Vol. 56. E. Norrby ed. pp 91–111, Karger, Basel), to recombinant gp120 produced insect cells infected with a baculovirus vector.

Example 3

Figure 4:
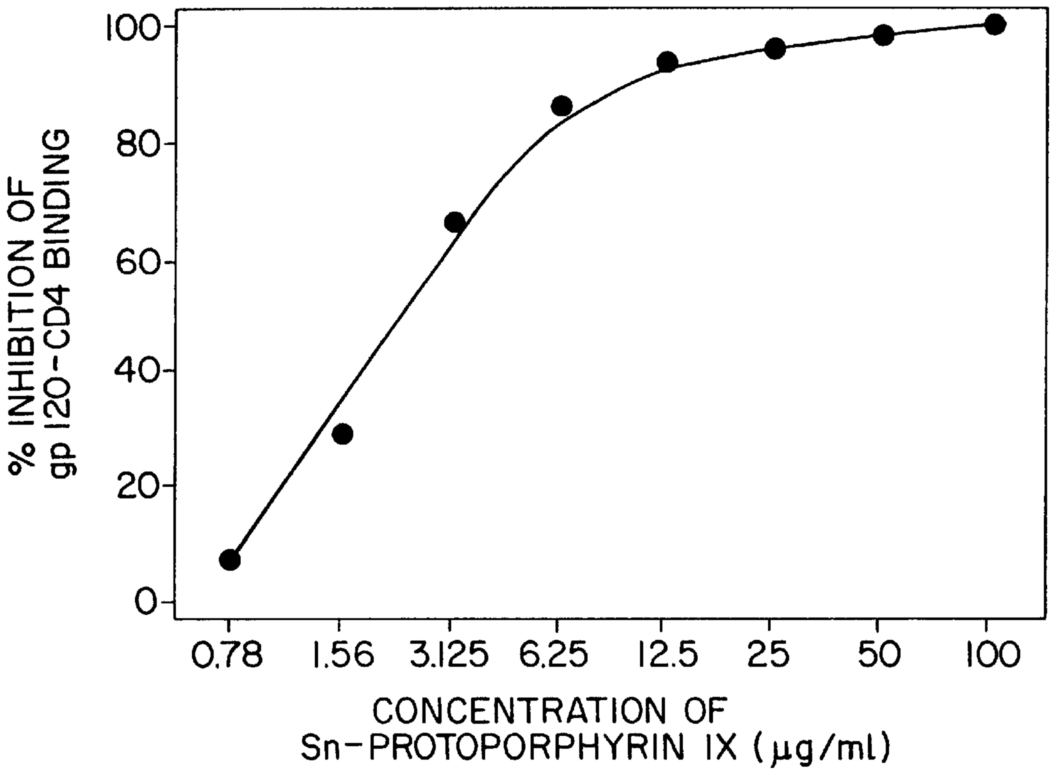
FIG. 4 is a graph which shows the inhibitory effect of tin protoporphyrin IX on the binding of recombinant gp120 (produced in insect cells infected with a baculovirus recombinant) to soluble CD4.

Determination of the Inhibitory Effect of Sn-PTP-IX on Binding to CD4 of gp120 and of Anti-CD4 mAbs The association between recombinant CD4 and gp120 and the inhibitory effect of Sn-PTP-IX on this association was measured by the Nenquest drug discovery (assay) system: HIV-1 gp120-CD4 receptor (catalog number NED-006; Du Pont NEN Research Products, Boston, Mass., USA). The results are depicted in FIG. 4, which shows that Sn-PTP-IX inhibits the association between gp120 and soluble CD4.

The binding of Sn-PTP-IX to the V3 loop of gp120 elicited allosteric effects resulting in inhibition of binding of gp120 of monoclonal antibodies specific for the CD4 binding site on gp120. This effect was not observed with a deletion mutant of gp120 lacking the V3 loop sequence. It is thus considered that Sn-PTP-IX can distort the native conformation of the HIV-1 envelope and thereby prevent infection.

It will be appreciated that the instant specification is set forth by way of illustration and not limitation, and that various modifications and changes may be made without departure from the spirit and scope of the present invention.

What is claimed is:

1. A method of preventing HIV-1 infection or HIV-2 infection comprising locally administering to a human a pharmaceutically effective anti-HIV-1 or anti-HIV-2 amount of a protoporphyrin alone or in admixture with a pharmaceutically acceptable diluent, said protoporphyrin being tin protoporphyrin IX or a pharmaceutically acceptable salt thereof.

2. The method of claim 1, wherein the human is a female and tin protoporphyrin IX is vaginally administered.

3. The method of claim 2, wherein tin protoporphyrin IX or a pharmaceutically acceptable salt thereof is administered prior to or during engaging in sexual intercourse.

4. The method of claim 2, wherein tin protoporphyrin IX or a pharmaceutically acceptable salt thereof is administered in the form of a vaginal cream, lotion, ointment, gel, paste, jelly, spray, solution, emulsion or foam.

5. The method of claim 4, wherein tin protoporphyrin IX or a pharmaceutically acceptable salt thereof is applied on a condom, a contraceptive diaphragm or a contraceptive sponge.

6. The method of claim 4, wherein HIV-1 infection is prevented.

7. The method of claim 6, wherein the HIV-1 is an isolate selected from the group consisting of IIIB, MN, RE, SF-2 and an isolate which replicates in the presence of AZT.

8. The method of claim 1, wherein the human is a human baby and tin protoporphyrin IX or a pharmaceutically acceptable salt thereof is topically administered to the baby after the birth of the baby.

9. The method of claim 1, wherein the human body is a female and tin protoporphyrin IX or a pharmaceutically acceptable salt thereof is vaginally administered to the female during or before childbirth.

10. The method of claim 1, wherein tin protoporphyrin IX is rectally administered.

11. A method of preventing HIV-1 infection or HIV-2 infection comprising administering to a human a pharmaceutically effective anti-HIV-1 or anti-HIV-2 amount of tin mesoporphyrin IX or a pharmaceutically acceptable salt thereof alone or in admixture with a pharmaceutically acceptable diluent.

12. A method of treating HIV-1 infection or HIV-2 infection comprising administering to a human a pharmaceutically effective anti-HIV-1 or anti-HIV-2 amount of a tin mesoporphyrin or a pharmaceutically acceptable salt thereof, alone or in admixture with a pharmaceutically acceptable diluent.

* * * * *